United States Patent [19]

Okun

[11] 3,987,202

[45] Oct. 19, 1976

[54] METHOD OF TREATING PSORIASIS

[76] Inventor: Milton R. Okun, 47 Commercial Wharf, Boston, Mass. 02110

[22] Filed: Dec. 23, 1974

[21] Appl. No.: 535,362

Related U.S. Application Data

[63] Continuation-in-part of Ser. No. 474,416, May 30, 1974, abandoned.

[52] U.S. Cl. .................................. 424/331; 424/28; 424/70; 424/233
[51] Int. Cl.² ...................... A01N 9/24; A61K 31/12
[58] Field of Search ............... 424/331, 60, 59, 262, 424/309

[56] References Cited
UNITED STATES PATENTS

3,856,934   12/1974   Kligman ............................... 424/62

OTHER PUBLICATIONS

Dyer, An Index of Tumor Chemotherapy, NIH, 3/1949, pp. 10 & 131.

Arman et al., Journal of Investigative Dermatology, 1949, vol. 12, pp. 11–17.

*Primary Examiner*—Dale R. Ore
*Attorney, Agent, or Firm*—Thompson, Birch, Gauthier & Samuels

[57]  ABSTRACT

This invention relates to the treatment of human skin by the use of melanins, in particular for the treatment of psoriasis.

8 Claims, 5 Drawing Figures

METHOD OF TREATING PSORIASIS

CROSS-REFERENCE TO RELATED APPLICATIONS

This application is a continuation-in-part of application Ser. No. 474,416 filed May 30, 1974 and now abandoned.

BACKGROUND OF INVENTION

Common skin disorders such as psoriasis, dermatitis, and eczema afflict large numbers of people each year. The prior art teaches a variety of medicinal and other lotions, creams, salves and ointments intended for external application to human skin and claimed to have a variety of beneficial properties ranging from merely moisturizing and cleansing to alleviating all manner of skin disorders. Exemplary of such prior art are U.S. Pat. Nos. 153,008; 1,525,285; and 3,016,334. None of these prior art compositions, however, has proved to be wholly satisfactory in treating skin disorders such as psoriasis, dermatitis and eczema. The *Merck Index* (7th ed. 1960) recognizes that coal tar in 3—5% ointment or 2% solution is useful in treating such diseases, but it cautions that prolonged skin contact can actually induce dermatitis and skin cancer. Topical corticosteroids have been used with varying success for treating psoriasis. With prolonged use under plastic occlusion they may result in atrophy of the skin.

Internal cytotoxic agents have also been used, but they have serious side-effects, including liver damage and bone marrow suppression.

Ultraviolet light is another useful method for treating psoriasis, and its effect can be increased by use of coal tar ointment or topical or internal psoralens. This approach usually requires repeated visits to the physician's office or an inpatient stay of several weeks. Thus, a safe and effective means for treating such skin lesions is still being sought.

Melanins are complex aggregate organic materials which are found naturally in skin, hair and eyes of mammals, in insect cuticle and in plants, or which may be produced synthetically from either dopa or quinone precursors as described in the *Merck Index*. A large variety of studies have been performed on the chemical nature and properties of melanins, two of the most complete and most recent reviews being Leon M. Edelstein, "Melanin: A Unique Biopolymer", in 1971 *Pathobiology* Annual 309-324 and Ralph D. Lillie, "Histochemistry of Melanins", in 1969 *Pigments in Pathology* 327-351, edited by M. Wolman. In general, melanins are best known for their skin and hair dyeing properties. For example, in U.S. Pat. No. 2,745,788, hydroquinone is oxidized to melanin and used to tint or dye hair. The therapeutic properties of melanins in treating skin diseases have not heretofore been recognized.

OBJECTS OF INVENTION

Accordingly, it is a primary object of this invention to provide compositions and methods for treating skin lesions using melanins.

It is another object of this invention to provide a method for synthetically preparing melanins which are particularly useful in treating skin lesions.

It is specifically an object of this invention to provide a method for treating psoriasis, dermatitis, eczema and similar skin disorders using melanins.

SUMMARY OF INVENTION

It has now been found that melanins, particularly those prepared in the special manner set forth herein, have utility in the therapeutic treatment of skin lesions of all types. Thus, while not necessarily effecting a perfect and permanent cure, the application of melanins to the skin by means of creams, lotions, ointments and the like has been found effective in alleviating the symptoms of psoriasis, seborrheic dermatitis, eczema, benign skin tumors such as warts, and other virus induced skin disorders. All types of inflammatory skin disorders and benign neoplasms of the surface epidermis, which are described further in Walter F. Lever's book entitled *Histopathology of the Skin* (1967), are intended to be included within the scope of this invention.

DESCRIPTION OF PREFERRED EMBODIMENT

Melanins are a class of compounds which are polymeric oxidation products of phenols or quinones. They react readily with proteins to form melanoproteins. As used herein, the term "melanin" is meant to include all biologic golden-brown to black organic substances that are polycyclic polymers of high molecular weight in which the chromophoric grouping is usually the quinone grouping.

Natural melanins in animals derive from the oxidation of tyrosine to indole quinone, which then polymerizes and combines with protein to form the final product (melanoprotein). Synthetic melanins which parallel the structure of natural melanins can be made by enzymatic oxidation of tyrosine or dopa or by auto-oxidation of dopa (dopa - dihydroxyphenylalanine). Synethic melanins of this type (dopa melanin) are only moderately soluble in water, even at alkaline pH.

Synethic melanins which are much more soluble in water can be prepared by the auto-oxidation of quinone (e.g., p-benezoquinone) or hydroquinone. Such quinone melanins are known in the art as humic acid-like substances. Similar synthetic substances called "synthetic humic acids" can be prepared from phenols or quinones by oxidation in alkaline solution with aerial oxygen. The auto-oxidation by which these melanins are prepared is very rapid at alkaline pH. In particular, it has been found that such quinone melanins are at least 18-30 times more soluble in an aqueous solution at a pH of about 9.0 and at room temperature than the corresponding dopa-derived melanins. At pH 9.5 or above the solubility differential is even greater; a 25% colloidal solution of quinone melanin has been obtained.

In the preferred practice of this invention, melanin is prepared by the auto-oxidation of quinone (p-benzoquinone) or hydroquinone in alkaline solution at a pH of at least about 9.0. The melanin thus prepared is employed in lotion, cream, or ointment form to treat psoriasis and other skin disorders.

Although the biochemical mechanism by which melanins are effective for treating psoriasis and other inflammatory disorders is not fully understood, one or more of the following biochemical reactions are believed to be involved: (a) melanins bind to peptides and proteins and thus interfere with nucleoprotein synthesis and protein synthesis, thereby inhibiting cellular-proliferative aspects of inflammation; (b) melanins bind to protein antigens and antibodies, thereby inhibiting antigen-antibody interactions which may be involved in inflammation; (c) melanins bind to amine and peptide mediators of inflammation; and, (d) melanins bind to and stabilize lysosomal membranes.

If the melanin is to be used in solution form, the mildly alkaline solution in which the auto-oxidation took place can be employed directly, for example by topical application with a cotton applicator three to seven times a day with or without subsequent occlusion of the treated area with a plastic dressing. Alternatively, the solution may be used to impregnate a gauze pad or bandage which is applied to the lesion and covered with a plastic dressing. The gauze pad impregnated with the solution may be allowed to dry out for storage and can be rehydrated just before use. Still another way of using the melanins of this invention is to evaporate the alkaline solution to dryness, pulverize the resulting reddish-brown to black colored cake in a blender, and mix the powder with a suitable cream or ointment base, such as a "Eucerin" cream containing about 10% water for added "creaminess", which can then be applied to the skin with or without occlusion with a plastic dressing. While the oxidation products of quinones are generally black in color, the hydroquinone oxidation products often have more of a reddish-brown color, possibly due to the presence of lower molecular weight humic acid-like substances. Generally, the lotion form was found to be slightly more effective than the cream; however, the effectiveness of both the lotion and the cream has been found to be increased by employing an overnight occlusion or pack with plastic film. Because the slightly alkaline nature of the lotion or cream has been found in some instances to cause irritation with occlusion, it is also within the scope of this invention to neutralize the alkaline solution of melanin with an acid, such as hydrochloric acid, to a pH of about 7.5 or to buffer the entire system at about pH - 7.5 using a conventional phosphate buffer.

Another beneficial variation in the practice of this invention is the inclusion of about 2 wt.-% (based on total composition weight) of salicylic acid in the lotion or cream. The salicylic acid has been found useful in promoting the penetration of dry skin scale in treating hyperkeratotic lesions, thereby facilitating bringing the active ingredient, the melanin, to the epidermis underneath.

EXAMPLE 1

Preparation of Agent

A beaker or other suitable container is fitted with an ice jacket. The ice jacket is not required although it is recommended because of the highly exothermic nature of the reaction.

6 grams of quinone or hydroquinone is gradually stirred into about 50 cc. of water. 10 N sodium hydroxide is added to the solution until the pH is about 9.5. Then water is added to make a final solution of about 6% quinone melanin. The solution turns rapidly black as auto-oxidation proceeds; it is allowed to stand for several days to insure complete auto-oxidation of the quinone.

The resulting alkaline solution of melanins may be used directly, either full strength or diluted, or neutralized to a pH of about 7.5 as described above. Alternatively, where a cream form is desired, the above solution is evaporated to dryness and the resultant melanin cake is pulverized in a "Waring" blender or similar device. A 6% cream can be made by mixing 5 gm. of the powder with 95 gm. of hydrated "Eucerin" cream (1 part water: 4 parts "Eucerin" cream) using a "Waring" blender. In this manner, creams or ointments having a composition consisting of about 2–10 wt.-% melanins can be prepared. It is not necessary in either case to separate or neutralize the sodium hydroxide or other alkaline material.

The following examples demonstrate the success of the present invention in treating psoriasis. Psoriasis is a common inflammatory disorder of the skin of unknown cause characterized by reddish plaques with a silvery scale. In psoriasis the following abnormalities are present: a) there is an increased proliferation of epidermal cells; b) there is an inflammatory infiltrate in the dermis; and, c) the capillaries in the upper dermis are dilated and tortuous.

EXAMPLE 2

The patient is a 30 year old female with longstanding psoriasis involving the extremities. Before treatment there were numerous large, erythematous, scaling plaques. FIG. 1 represents elbow lesion one week after beginning treatment three to seven times a day with 6% quinone melanin solution. Scaling and erythema have been reduced, but the extent of original plaque is still evident. Slight stain from melanin can also be seen.

FIG. 2 represents appearance of the same elbow after three weeks of additional treatment. Some small scaling areas remain at the periphery of the original lesion and at the apex of the elbow, but large areas of normal-appearing skin are now present within the area of the original plaque. Moreover, during the course of treatment, the considerable itching experienced by the patient before treatment was substantially reduced.

EXAMPLE 3

The patient is an 18 year old female with mild psoriasis of the elbows for about one year. FIG. 3 represents a small scaling, erythematous plaque area before treatment.

EXAMPLE 4

Figure 1:
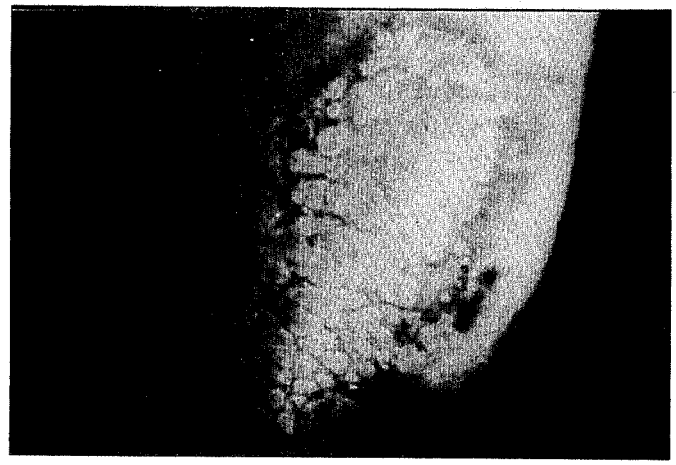
Figure 2:
Figure 3:
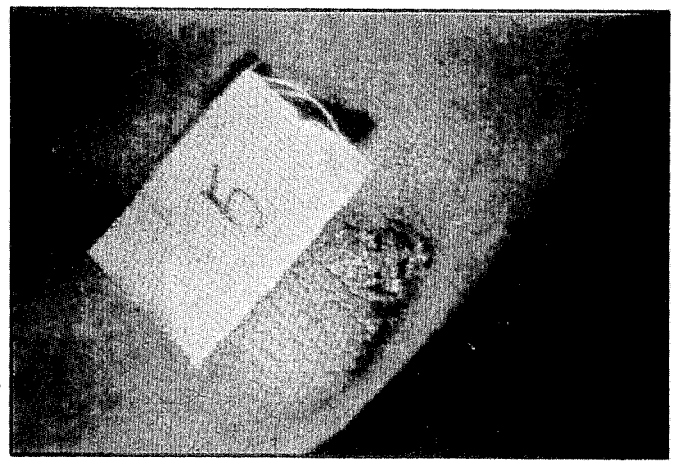
Figure 4:
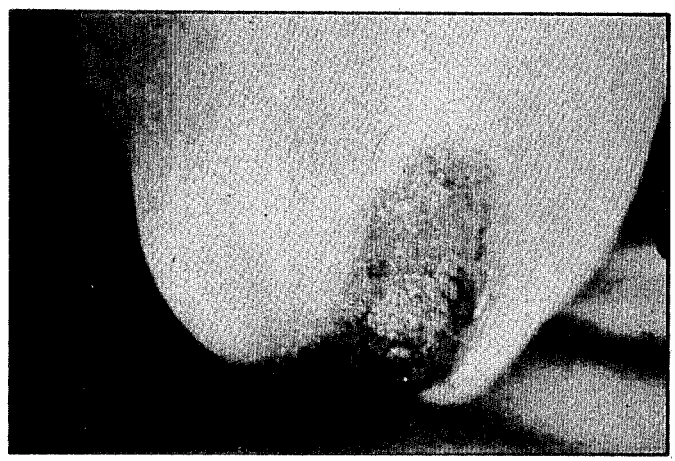
FIG. 4 shows the appearance of the same lesion after one week of treatment, three times a day, with 6% quinone melanin solution. Scaling is reduced, but the melanin stain obscures erythema.
Figure 5:
FIG. 5 shows the appearance of the lesion after one additional week of treatment. Scaling and erythema are virtually gone although slight thickening of the skin remains.

The following was a group study of ten patients with psoriasis. They had an age range of 18 to 32; eight were females and two were males. Two of the patients had, in addition to psoriasis, lesions of serborrheic dermatitis, another inflammatory skin disorder of unknown cause, characterized by more diffuse inflammatory patches and scaling.

Treatment consisted of topical application of the quinone melanin lotion or cream three to seven times a day. In some instances the preparations were also applied at bedtime and, in these cases, the treated lesions were occluded with plastic film overnight.

In all cases, the lesions of psoriasis were rapidly suppressed by topical application of quinone melanin lotion or cream. Improvement was usually noted within one or two days. Total suppression of lesions in milder cases was observed usually within a few weeks and in more severe cases within 12 weeks. No toxic or irritant reactions were observed. When treatment was stopped, the remission lasted for periods ranging from 10 days to 16 weeks.

Lesions of seborrheic dermatitis cleared more rapidly than lesions of psoriasis. Total suppression was generally noted within several days.

The lotion was found to be more effective than the cream. Occlusion with plastic film overnight enhanced effectiveness of both the lotion and the cream.

Although all cases tested have shown benefit from treatment with melanins, in cases of acute eruptive psoriasis, patients have shown a slower rate of responsiveness. It is well known, however, that acute eruptive psoriasis is more refractory to treatment of any type than more stable forms of psoriasis.

Having thus described the invention, what is claimed is:

1. The method of treating psoriatic human skin comprising the step of applying melanin to the afflicted skin area in an effective amount sufficient to treat the psoriatic condition.

2. The method of treating psoriatic human skin comprising the step of applying melanin in an alkaline solution to the afflicted skin area in an effective amount sufficient to treat the psoriatic condition.

3. The method of treating psoriatic human skin comprising the step of applying melanin in a buffered solution having a pH of about 7.5 to the afflicted skin area in an effective amount sufficient to treat the psoriatic condition.

4. The method of treating psoriatic human skin comprising the step of applying melanin in a cream form to the afflicted skin area in an effective amount sufficient to treat the psoriatic condition.

5. The method of claim 1 wherein said melanin is applied in combination with an amount of about 2% by weight of salicylic acid.

6. The method of claim 1 wherein said melanin is synthetically prepared.

7. The method of claim 6 wherein said melanin is applied in an aqueous solution containing about 6% by weight of melanin.

8. The method of claim 1 wherein the treated skin area is occluded overnight.

* * * * *